United States Patent
Hendriks et al.

(10) Patent No.: US 9,468,379 B2
(45) Date of Patent: Oct. 18, 2016

(54) DETERMINATION OF A LIPID WATER RATIO

(75) Inventors: Bernardus Hendrikus Wilhelmus Hendriks, Eindhoven (NL); Jeroen Jan Lambertus Horikx, Eindhoven (NL); Gerhardus Wilhelmus Lucassen, Eindhoven (NL); Rami Nachabe, Eindhoven (NL); Marjolein Van Der Voort, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 524 days.

(21) Appl. No.: 13/641,229

(22) PCT Filed: Apr. 18, 2011

(86) PCT No.: PCT/IB2011/051662
§ 371 (c)(1),
(2), (4) Date: Oct. 15, 2012

(87) PCT Pub. No.: WO2011/132128
PCT Pub. Date: Oct. 27, 2011

(65) Prior Publication Data
US 2013/0026367 A1    Jan. 31, 2013

(30) Foreign Application Priority Data

Apr. 21, 2010 (EP) .................................... 10160576

(51) Int. Cl.
*G01N 21/359* (2014.01)
*A61B 5/00* (2006.01)

(52) U.S. Cl.
CPC ........... *A61B 5/0059* (2013.01); *A61B 5/4869* (2013.01); *G01N 21/359* (2013.01)

(58) Field of Classification Search
CPC . A61B 5/0059; A61B 5/4869; G01N 21/359
See application file for complete search history.

(56) References Cited

U.S. PATENT DOCUMENTS

| 4,805,623 A | 2/1989 | Jobsis |
| 6,587,702 B1 | 7/2003 | Ruchti et al. |

(Continued)

FOREIGN PATENT DOCUMENTS

| BE | 1017986 A3 | 3/2010 |
| CN | 1424888 A | 6/2003 |

(Continued)

OTHER PUBLICATIONS

Scampoli et al., "Application of Monte Carlo technique to time-resolved transillumination: a comparison with experimental data," Proc. Spie 3195, Laser-Tissue Interaction, Tissue Optics and Laser Weling III, 246, (Jan. 14, 1998). Retrieved from internet <http:doi.10.1117/12.297908>; Retrieved [Sep. 23, 2014].*

(Continued)

*Primary Examiner* — Yara B Green

(57) ABSTRACT

The present invention relates to an apparatus, a method and a computer program for determining a lipid-water ratio and a scattering parameter of a sample. In particular, the invention relates to an apparatus comprising a light source and a detector arranged to measure an optical parameter at various wavelengths, where the wavelengths are selected so that at two of the wavelengths the absorption coefficients for both water and lipids are substantially identical. This enables determination of a scattering parameter. A further measurement at a third wavelength enables determination of a water-lipid ratio. According to a specific embodiment, the light source and the detector are arranged in relation to an interventional device, so as to be able to examine a tissue in terms of lipid-water ratio and scattering during an intervention.

15 Claims, 6 Drawing Sheets

(56) References Cited

U.S. PATENT DOCUMENTS

| | | |
|---|---|---|
| 7,486,985 B2 | 2/2009 | Marshik-Geurts et al. |
| 7,898,649 B2 | 3/2011 | Masumura |
| 2002/0084417 A1 | 7/2002 | Khalil et al. |
| 2003/0220548 A1 | 11/2003 | Schmitt |
| 2006/0058683 A1 | 3/2006 | Chance |
| 2007/0118027 A1 | 5/2007 | Baker et al. |
| 2008/0076983 A1* | 3/2008 | Debreczeny ......... A61B 5/0059 600/310 |
| 2008/0221409 A1* | 9/2008 | Hoarau ......................... 600/310 |
| 2008/0221416 A1* | 9/2008 | Baker ..................... A61B 3/10 600/318 |
| 2009/0069653 A1 | 3/2009 | Yoshida et al. |
| 2009/0306520 A1 | 12/2009 | Schmitt |
| 2010/0004517 A1 | 1/2010 | Bryenton et al. |
| 2010/0052674 A1* | 3/2010 | Jellus et al. .................. 324/309 |

FOREIGN PATENT DOCUMENTS

| | | |
|---|---|---|
| CN | 101292875 A | 10/2008 |
| CN | 101341391 A | 1/2009 |
| CN | 101526465 A | 9/2009 |
| JP | 06317520 A | 11/1994 |
| JP | 07270309 A | 10/1995 |
| JP | 2003329581 A | 11/2003 |
| JP | 2004081427 A | 3/2004 |
| JP | 2004138454 A | 5/2004 |
| WO | 2008058014 A2 | 5/2008 |
| WO | 2009153719 A1 | 12/2009 |

OTHER PUBLICATIONS

T. Troy et al., "Optical Properties of Human Skin in the Near Infrared Wavelength Range of 1000 to 200 nm", Journal of Biomedical Optics, SPIE—International Society for Optical Engineering, US, vol. 6, No. 2, Apr. 1, 2011, pp. 167-176.

G. Zonios et al., "Comparative Evaluation of Two Simple Diffuse Reflectance models for Biological Tissue Applications", Applied optics, Optical Society of America, Washington, DC, US, vol. 47, No. 20 Sep. 2008, pp. 4965-4973.

Mlcek, J. et al. "Application of FT NIR spectroscopy in the determination of basic chemical composition of pork and beef", Czech Journal of Animal Science, vol. 51, Issue 8, 2006, pp. 361-368.

* cited by examiner

DETERMINATION OF A LIPID WATER RATIO

FIELD OF THE INVENTION

The present invention relates to an apparatus for determination of parameters related to a chemical composition of a sample, and more specifically to an apparatus, a method and a computer program for determination of a lipid-water ratio and scattering in a sample.

BACKGROUND OF THE INVENTION

Determining the type of tissue in front of an interventional device is important to improve the outcome of an intervention. For instance in the case of oncology the procedure of taking a biopsy would improve if the tip of the biopsy needle is for certain in the suspected tissue. Also during surgery finding the boundaries of the tumor on the spot would greatly improve the surgical outcome. Another application is detection of the quality of the food. For instance a simple device indicating the lipid content and the "freshness" would be of help in various situations for consumers in daily life.

Determining a lipid-water ratio and scattering in a sample is desirable in a number of applications. One such application is the detection of quality of food. An apparatus for determination of a lipid-water ratio could also be advantageous for monitoring a lipid-water ratio in an animal or a human. Current apparatus capable of determining a lipid-water ratio and scattering in a sample might be complex to use, time consuming and/or expensive. There exist apparatuses that can measure the constitution of the samples. For instance, a spectrometer measuring in the near infrared (NIR) range can measure the reflectance spectra from which water and fat can be deduced. However, this apparatus is not simple, compact or low-cost. For many applications, such as for home applications, a compact, simple, and low-cost apparatus for determining a lipid-water ratio and/or a scattering parameter in a sample could be advantageous.

The reference U.S. Pat. No. 7,486,985 B2 relates to methods and devices for characterizing tissue in vivo, e.g., in walls of blood vessels, to determine whether the tissue is healthy or diseased. The reference, however, does not describe a simple apparatus for determining a lipid-water ratio and/or a scattering parameter in a sample.

Hence, an improved apparatus for determining a lipid-water ratio and/or a scattering parameter in a sample would be advantageous, and in particular a simple, compact and in principle low cost apparatus for determining a lipid-water ratio and/or a scattering parameter in a sample would be advantageous.

SUMMARY OF THE INVENTION

The present invention preferably seeks to alleviate or eliminate the above-mentioned disadvantages of determining a lipid-water ratio and/or scattering in a sample. In particular, it may be seen as an object of the present invention to provide an apparatus, a method and a computer program which are capable of determining a lipid-water ratio and/or a scattering parameter in a simple, compact and cost-efficient way.

It is a further object of the present invention to provide an alternative to the prior art.

Thus, the above described object and several other objects are intended to be obtained in a first aspect of the invention by providing an apparatus for determining a lipid-water ratio in an associated sample, comprising a light source, and a light detector, the light source and the light detector being arranged to measure an optical parameter of the sample at a limited number of selected and distinct wavelengths, and arranged to measure a first, second and third optical parameter at the selected and distinct wavelengths lambda_1, lambda_2 and lambda_3, respectively, wherein an optical absorption coefficient for water at lambda_1 is substantially similar to an optical absorption coefficient for water at lambda_2 and an optical absorption coefficient for lipids at lambda_1 is substantially similar to an optical absorption coefficient for lipids at lambda_2, and wherein the apparatus is capable of determining a lipid-water ratio of the sample based on the first and second optical parameters measured at lambda_1 and lambda_2 and the third optical parameter measured at lambda_3.

The invention is particularly, but not exclusively, advantageous for determining a lipid-water ratio and/or a scattering parameter in a sample in a simple, compact and cost-efficient way. As the invention enables the determination of a lipid-water ratio and/or a scattering parameter in a sample using a limited number of selected and distinct wavelengths, a compact, simple, and in principle low cost apparatus might be devised. Furthermore, it might enable omission of expensive spectrometers, which spectrometers are capable of measuring spectra of samples. Furthermore, in some embodiments, the invention might lead to relatively fast measurements, since a lipid-water ratio and/or a scattering parameter in a sample may be determined using only measurements at a limited number of selected and distinct wavelengths, and since the selected and distinct wavelengths enables a relatively straightforward deduction of the lipid-water ratio and/or the scattering parameter in the sample.

It is to be understood that "wavelengths" include "narrow wavelength intervals". Furthermore, the expression "substantially similar to" is understood to include both the mathematically abstraction of exact similarity as well as an interval around the stated value, such as an interval corresponding to an experimental uncertainty. In this context, the experimental uncertainty denotes an uncertainty in terms of the wavelength, but also in terms of other parameters, such as the intensity, since an uncertainty in the measured intensity translates to an interval of wavelengths, which size at a certain wavelength depends on the slope of the measured intensity with respect to wavelength at that particular wavelength. The expression "substantially similar to" is further understood to include a relative deviation, such as a relative numerical deviation of 0.01%, 0.1%, 1.0%, 5.0% or to include an absolute deviation, such as an absolute numerical deviation of 0.1 nm, 1.0 nm or 10 nm.

Optical parameter is understood to be light intensity at the detector. Configurations in which this can be measured include: (1) diffuse reflectance, i.e., the source and the detector are at the same side, (2) transmission measurement, i.e., the tissue is for instance sandwiched between source and detector. However, other configurations are also possible.

The measurement of the optical parameter can be carried out in various ways, such as by means of various filter systems at different positions in the optical path, light sources emitting in different wavelength bands, or detectors for different wavelength bands. This is further elaborated below.

The sample may be any sample, such as a tissue or a sample of foodstuffs.

There exist apparatuses that can measure the constitution of the samples, but they are not simple and easy to use. For instance a spectrometer in the NIR can measure the reflectance spectra from which water and lipids can be deduced (cf., FIG. 1). Because of the expensive detector array, such as an InGaAs detector array, this is not a low-cost apparatus. The InGaAs detector arrays are rather expensive now. A point detector is much cheaper. In an embodiment of the invention, a point detector, such as an InGaAs point detector, is used. This might make the apparatus cheaper.

The invention can be used in the field of oncology, or other healthcare applications where the determination of lipid-water ratio and scatter is important. Furthermore, it can be used in the food industry. In these applications, the lipid-water ratio, as well as the amount of scattering, is an important parameter to be determined.

In a particularly useful embodiment, the apparatus is further arranged to access a database comprising information regarding various tissue types, and identify which tissue type or tissue types the sample is most likely to comprise, and wherein the identification is based on the lipid-water ratio. An advantage of this is that valuable information regarding the tissue type might be obtained this way. In an alternative embodiment, the database comprises information regarding foodstuffs in general, i.e. both from animals (and derived there from, e.g. milk and cheese) and vegetables (e.g. nuts and other lipid containing raw materials).

In another embodiment of the invention, the first selected wavelength lambda_1 and the second selected wavelength lambda_2 are chosen so as to enable disentangling of the contributions to the optical parameter from scattering and absorption. This may be advantageous in that both scattering and absorption are parameters of interest, however, only if they can be disentangled so that measurement of one parameter is not obstructed by the other.

In yet another embodiment, the apparatus is further capable of determining a scattering parameter via a direct relation between the scattering parameter and the first and second optical parameters. Using a direct relation between the scattering parameter, to be determined, and the first and second optical parameters may be advantageous since a direct relation, such as a mathematical function or a look-up table, may be relatively fast to use. Another possible advantage is that the scattering parameter may be determined quantitatively. Yet another possible advantage is that the scattering parameter might be determined unambiguously. This particular embodiment may thus be faster and less ambiguous, compared to, for example, a fitting procedure which may include a non-direct relation between a scattering parameter and the first and second optical parameters.

In another embodiment, the apparatus is further capable of determining a parameter indicative of freshness based on the scattering parameter. It has been determined by the present inventors, that various samples containing lipids in a medium containing water are emulsion like. The quality of the emulsion changes in time and will eventually lead to changes in the size of the emulsion vesicles. This will have a strong effect on the scattering parameter that is linked to the size of the emulsion vesicles. Thus, a possible advantage of this particular embodiment is that the freshness of a sample can be assessed. In the present context, freshness is understood to be a parameter indicative of how well the original qualities of a sample have been retained. Thus, a sample is expected to originally have a high degree of freshness, which is degraded over time. The degradation of freshness may depend on a number of factors, such as time, original quality, and storage conditions. The freshness may be a parameter of importance in a number of applications. In particular the freshness may be relevant for assessing a quality of foodstuffs.

In still another embodiment, the apparatus further comprises a plurality of light sources with different wavelength bands and/or a plurality of light detectors with different wavelength bands, wherein two of the wavelength bands correspond to lambda_1 and lambda_2. An advantage of having a plurality of light sources with different wavelength bands might be that the selection of wavelengths are given by the light sources, and consequently neither broad band light source nor filter is required. Another possible advantage is that a relatively cheap, simple and compact apparatus might be enabled. Similarly, a plurality of light detectors with different wavelength bands might enable use of a single broad band light source without use of a filter between light source and detector. The light sources may include Light Emitting Diodes (LED's) or laser sources.

In another embodiment, the apparatus further comprises a processor arranged for receiving information derived from the first optical parameter measured at lambda_1, receiving information derived from the second optical parameter measured at lambda_2, receiving information derived from the third optical parameter measured at lambda_3, calculating a scattering parameter based on the information derived from the first optical parameter and the information derived from the second optical parameter, and calculating a lipid-water ratio based on information derived from the scattering parameter and information derived from the third optical parameter. An advantage of including a processor might be that calculations might then be conducted in less time, automatically and more reliably.

In yet another embodiment, the wavelengths lambda_1 and lambda_2 are chosen to be substantially identical to any one of the sets of wavelengths {740.0 nm; 773.0 nm}, {955.0 nm; 1000.0 nm}, {1010.0 nm; 1128.5 nm}, {1150.5 nm; 1251.0 nm}, or {1380.9 nm; 1663.9 nm}. By meticulously measuring the absorption spectra for water and lipids, respectively, and examining the spectra, these specific sets of wavelengths have been identified as sets of wavelengths which satisfy that an optical absorption coefficient for water at lambda_1 is substantially similar to an optical absorption coefficient for water at lambda_2 and an optical absorption coefficient for lipids at lambda_1 is substantially similar to an optical absorption coefficient for lipids at lambda_2.

In another embodiment, the light source and the light detector are arranged in relation to an interventional device, so as to be able to determine a lipid-water ratio of a sample in the vicinity of the interventional device. The interventional device may be any one of an endoscope, a biopsy needle, a catheter or the like. This embodiment may be advantageous for minimally invasive procedures.

In still another embodiment, the apparatus is arranged for measuring an optical parameter at four different wavelengths including lambda_1, lambda_2 and lambda_3. If four points are measured, a better compensation for non-linear effects can be made, and consequently, the result may be more accurate. It is noted, that further measurements, including measurements at other wavelengths, might further improve the accuracy.

According to a second aspect of the invention, the invention further relates to a method the method comprising the steps of measuring a first optical parameter at a first selected and distinct wavelength lambda_1, measuring a second optical parameter at a second selected and distinct wavelength lambda_2, measuring a third optical parameter at a third selected and distinct wavelength lambda_3, and determining a scattering parameter based on the first optical parameter and the second optical parameter, and determining a lipid-water ratio based on the scattering parameter and the third optical parameter wherein an optical absorption coefficient for water at lambda_1 is substantially similar to an optical absorption coefficient for water at lambda_2 and an optical absorption coefficient for lipids at lambda_1 is substantially similar to an optical absorption coefficient for lipids at lambda_2.

In another embodiment, the method further comprises the step of measuring a fourth optical parameter at a fourth selected and distinct wavelength lambda_4, the fourth optical parameter also being used in the step of determining a lipid-water ratio, wherein the third wavelength lambda_3 has substantially the same absorption coefficient for water as the absorption coefficient for water at lambda_1 and lambda_2, and the absorption coefficient for lipids at lambda_4 is substantially the same as the absorption coefficient for lipids at lambda_1 and lambda_2. By choosing four wavelengths fulfilling the above described criteria, it is expected, that a sample on which measurements are conducted and where a straight line intercepts lambda_1, lambda_2 and lambda_3 contains no lipids. Correspondingly, if the line intercepts lambda_1, lambda_2 and lambda_4, it is expected that the sample contains no water.

In a still further embodiment, the set of wavelengths lambda_1, lambda_2, lambda_3 and lambda_4 are substantially identical to the set of wavelengths {1150.5 nm; 1251.0 nm; 1274.0 nm; 1360.0 nm}. By meticulously measuring the absorption spectra for water and lipids, respectively, this particular set of wavelengths has been identified as a set of wavelengths fulfilling that an optical absorption coefficient for water at lambda_1 is substantially similar to an optical absorption coefficient for water at lambda_2 and an optical absorption coefficient for lipids at lambda_1 is substantially similar to an optical absorption coefficient for lipids at lambda_2 and that the third wavelength lambda_3 has substantially the same absorption coefficient for water as the absorption coefficient for water at lambda_1 and lambda_2, and the absorption coefficient for lipids at lambda_4 is substantially the same as the absorption coefficient for lipids at lambda_1 and lambda_2.

In another embodiment of the invention, a method according to any one of claims the lipid-water ratio is determined using any one of the steps of:

inserting measured optical parameters into a look-up table, measuring further optical parameters and fitting a model to a number of the measured optical parameters, wherein the model includes the lipid-water ratio as an input parameter, comparing a number of the measured optical parameters with an analytical approximation based on diffusion theory, and/or comparing a number of the measured optical parameters with the result of a Monte Carlo calculation. An advantage of any one of these steps might be that it can be automated and that it may yield a faster and/or more precise determination of the lipid-water ratio.

According to a third aspect of the invention, a computer program is provided, that computer program product being adapted to enable a computer system comprising at least one computer having data storage means associated therewith to operate a processor arranged for receiving information derived from a first optical parameter, receiving information derived from a second optical parameter, receiving information derived from a third optical parameter, calculating a scattering parameter based on the information derived from the first optical parameter and the information derived from the second optical parameter, and calculating a lipid-water ratio based on information derived from the scattering parameter and information derived from the third optical parameter.

According to a fourth aspect of the invention, the invention further relates to a system for determining a lipid-water ratio in an associated sample, comprising an apparatus according to the first aspect, the system further comprising a database comprising information regarding a lipid-water ratio of the sample. The database may further comprise information regarding various tissue types, so as to enable determination of which tissue type or tissue types the sample is most likely to comprise. The database may alternatively comprise information regarding foodstuffs in general, i.e. both from animals (and foodstuffs derived there from, e.g. milk and cheese) and vegetables (e.g. nuts and other lipid containing raw materials).

The first, second, third and fourth aspect of the present invention may each be combined with any of the other aspects. These and other aspects of the invention will be apparent from and elucidated with reference to the embodiments described hereinafter.

BRIEF DESCRIPTION OF THE DRAWINGS

The apparatus, method and computer program for determination of a lipid-water ratio and a scattering according to the invention will now be described in more detail with regard to the accompanying figures. The figures show one way of implementing the present invention and is not to be construed as being limiting to other possible embodiments falling within the scope of the attached claim set.

In the drawings.

DETAILED DESCRIPTION OF THE EMBODIMENTS

Figure 2:
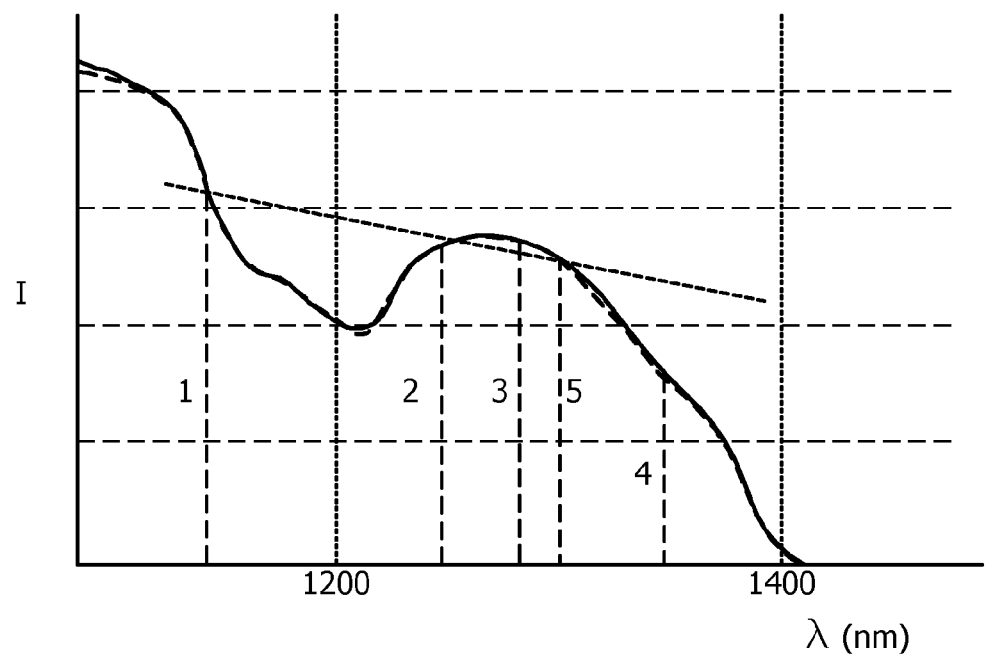
FIG. 2 shows an example of a part of the spectrum with four measurement positions used to derive the lipid/water ratio as well as the scattering parameter.

An apparatus containing a light source and a detector is described. In an exemplary embodiment the detector is capable of detecting the amount of light in at least four narrow well defined wavelength bands, while the wavelength range of the source is sufficiently broad to cover all of these narrow wavelength bands. Alternatively, the source is able to emit light in these narrow wavelength bands, while the detector response is sufficiently broad to cover all of the narrow wavelength bands. Let the wavelength positions be substantially located at the following positions: (1) 1150.5 nm, (2) 1251 nm, and two positions (3) and (4) in the wavelength band 1260-1400 nm. The measured intensities at these locations are $S_1$, $S_2$, $S_3$ and $S_4$, corresponding to wavelengths lambda_1, lambda_2, lambda_3 and lambda_4. An exemplary spectrum where the wavelengths have been marked is shown in FIG. 2, where the vertical axis shows wavelength ($\lambda$) in nanometers (nm) and the horizontal axis shows intensity (I) in arbitrary units.

The reflected intensity depends on both the scattering as well as the absorption in a nonlinear way. To disentangle these two we proceed as follows. At wavelength (1) and (2) the absorption coefficient of water and lipids can be found in Table I below.

TABLE I

Table of the absorption coefficient of water and lipids at various wavelengths.

| Point | wavelength nm | $\mu_a$(water) cm$^{-1}$ | $\mu_a$(lipids) cm$^{-1}$ |
|---|---|---|---|
| S1 | 1150.5 | 1.0500 | 0.2305 |
|  | 1195.5 | 1.2456 | 1.2469 |
|  | 1222.0 | 1.1595 | 1.1565 |
| S2 | 1251.0 | 1.0525 | 0.2386 |
| S3 | 1274.0 | 1.0517 | 0.1253 |
| S4 | 1360.0 | 3.6404 | 0.2373 |

From Table I we find that the absorption coefficient of water and lipids are substantially the same at 1150.5 nm and 1251.0 nm. Hence, independently of the water and lipid concentration, the amounts of absorption at these two wavelengths are the same. As a result the difference in the reflected intensity is purely due to scattering. The slope Q due to scattering in the reflectance spectrum near this region can thus be determined by $$Q = \frac{S_2 - S_1}{100.5 S_1} \quad (1)$$

The spectral shape due to scattering in this region can to a good approximation be described as a linear relation. To determine the lipid-water ratio we proceed as follows. Take the intensity at point $S_2$. Extrapolate this point using the slope until it intercepts with the spectrum between 1274 nm and 1360 nm. Note that according to Table I we expect the line to intercept at 1274 nm when it contains no lipids and at 1360 nm when it contains no water. Since we have corrected for the scattering, at this interception point the amount of absorption is the same as that at $S_2$ hence we find $$\mu_a^w(\lambda_2)w + \mu_a^l(\lambda_2)l = \mu_a^w(\lambda_5)w + \mu_a^l(\lambda_5)l \quad (2)$$

By comparing points in the spectrum with the same amount of absorption we circumvent the difficulty of the nonlinear dependence of the absorption on the spectrum. So $$\frac{l}{w} = \frac{\mu_a^w(\lambda_5) - \mu_a^w(\lambda_2)}{\mu_a^l(\lambda_2) - \mu_a^l(\lambda_5)} \quad (3)$$

To determine the interception point $S_5$ we proceed as follows. In one embodiment the intensity between the two measured points $S_3$ and $S_4$ are interpolated using a look-up table. This look-up table depends on the lipid-water ratio. The interception point $S_5$ is first derived using that the water content is 100%. The above will then yield a lipid/water ratio that may indicate different water content than the 100% assumed above. Adjust the look-up table by now using the new derived ratio. Repeat these steps until the amount found by the fitting procedure is in accordance with the assumed lipid/water ratio. In another embodiment we make use of an analytical approximation based on diffusion theory. Another embodiment is that the spectrum is measured between these two points. In yet another embodiment the missing part of the spectrum is determined by Monte Carlo calculation of the diffusion process of the photons inside the turbid media. Preferably, the two points $S_3$ and $S_4$ are taken substantially equal to 1274 nm and 1360 nm, respectively.

Figure 1:
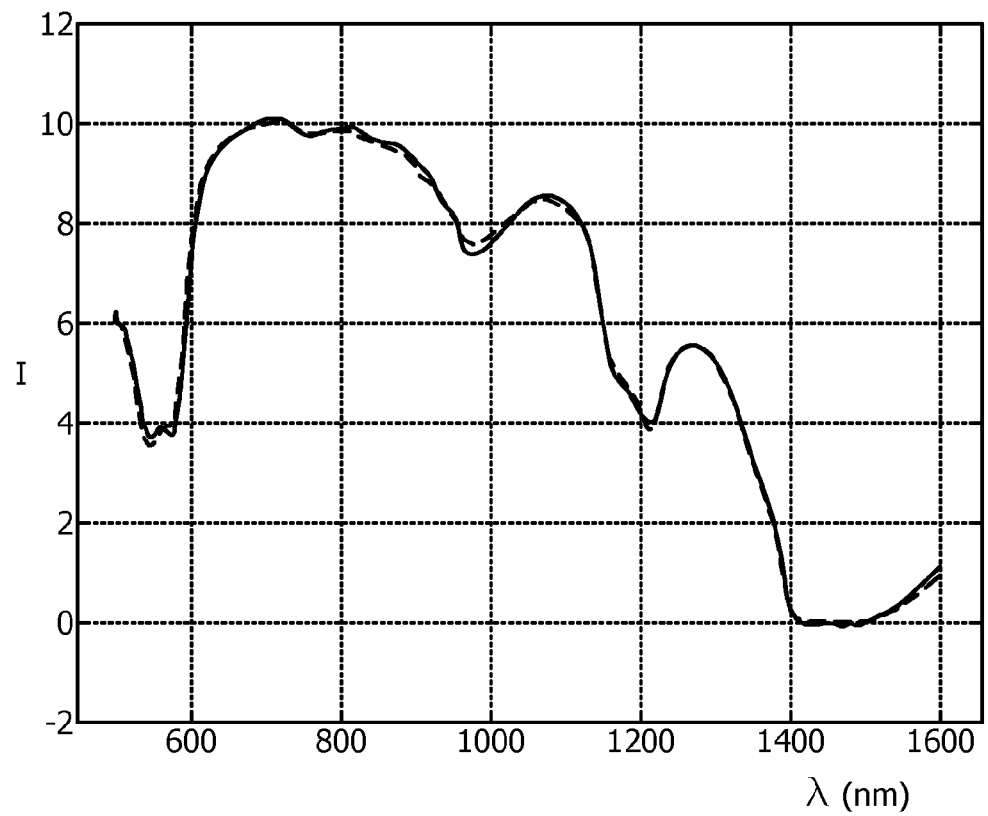
FIG. 1 shows an example of a measured spectrum of a fatty tissue (full drawn line). A model fit of the spectrum is also shown (dashed line)

FIG. 1 shows an example of a measured spectrum of a fatty tissue (full drawn line). A model fit of the spectrum is also shown (dashed line). The vertical axis shows wavelength ($\lambda$) in nanometers (nm) and the horizontal axis shows intensity (I) in arbitrary units.

Alternative Embodiment 1

In the first alternative embodiment we consider the system and algorithm as described above. We determine diffuse reflectance at the above four points. In this particular embodiment, the points $S_1$ and $S_2$ are measured at wavelength substantially equal to 1150.5 nm and 1251.0 nm, respectively. This allows us to remove the effect of scattering without having to know the absorption. To interpolate the values between measurement 3 and 4 we proceed as follows. From the measurement of the first two points we determined the scattering slope. The difference between the two measurements 3 and 4 is corrected for this scattering contribution. The remaining change is due to absorption effects. Between these two points 3 and 4 we assume that the contribution due to absorption can be approximated by being linear proportional to the absorption coefficient. Hence we can write:

$$S(\lambda, lw) = S_3 + (S_2 - S_1)\frac{(\lambda - \lambda_3)}{(\lambda_2 - \lambda_1)} + \left(S_4 - S_3 - (S_2 - S_1)\frac{(\lambda_4 - \lambda_3)}{(\lambda_2 - \lambda_1)}\right) \quad (4)$$

$$\left(\frac{(\mu_a^w(\lambda) + \mu_a^l(\lambda)lw) - (\mu_a^w(\lambda_3) + \mu_a^l(\lambda_3)lw)}{(\mu_a^w(\lambda_4) + \mu_a^l(\lambda_4)lw) - (\mu_a^w(\lambda_3) + \mu_a^l(\lambda_3)lw)}\right)$$

In Table II the results of the various methods to determine the lipid water ratio are listed when applied to various reference spectra. Method 1 (cf. Table II) corresponds to the method described by the embodiment above where the spectrum between point S3 and S4 are known and serves as a reference. Method 2 (cf. Table II) corresponds to the method as described in this first alternative embodiment. For low values of lipids the algorithm becomes inaccurate and gives rise to negative values. We should therefore round off negative values to zero lipid concentrations and similarly round off values larger than 1 to 1. From Table II we see that method 1 gives a good approximation of the lipid water ratio except for low values of lipids (below 15%). For method 2 the same holds as for method 1 with a slightly increased inaccuracy.

TABLE II

Comparison between the lipid/water ratio determined by the full spectral fit and the new proposed algorithms.

| Tissue | water | lipids | lipids/ (water + lipids) | meth. 1 | meth. 2 | meth. 3 | meth. 4 | meth. 5 | Δmeth. 1 | Δmeth. 2 |
|---|---|---|---|---|---|---|---|---|---|---|
| subcutaneous fat | 12 | 90 | 0.88 | 0.86 | 1.13 | −2.58 | 0.40 | 0.90 | 0.02 | 0.12 |
| fascia above | 53 | 18 | 0.25 | 0.12 | 0.17 | 0.09 | 0.08 | 0.17 | 0.13 | 0.13 |
| intrapinous ligament | 100 | 8 | 0.07 | −0.09 | −0.11 | −0.05 | −0.01 | −0.10 | 0.07 | 0.07 |
| muscle1 | 74 | 4 | 0.05 | −0.24 | −1.41 | −0.07 | −0.03 | −1.88 | 0.05 | 0.05 |
| Bone | 58 | 0 | 0.00 | −0.36 | 0.05 | −0.06 | −0.02 | −9.19 | 0.00 | 0.05 |
| inside intraspinous ligament | 34 | 41 | 0.55 | 0.44 | 0.56 | 0.61 | 0.21 | 0.51 | 0.11 | 0.01 |
| ligamentum flavum outerpart | 50 | 37 | 0.43 | 0.39 | 0.46 | 0.33 | 0.16 | 0.46 | 0.04 | 0.03 |
| in epidural space | 33 | 95 | 0.74 | 0.76 | 0.85 | −7.64 | 0.35 | 0.83 | 0.02 | 0.02 |
| Ligamentum | 49 | 68 | 0.58 | 0.63 | 0.70 | 0.85 | 0.23 | 0.73 | 0.05 | 0.12 |
| muscle2 | 91 | 7 | 0.07 | −0.16 | −0.47 | −0.05 | −0.01 | −0.46 | 0.07 | 0.07 |
| epidural fat | 26 | 72 | 0.73 | 0.73 | 0.52 | −3.71 | 0.38 | 0.80 | 0.00 | 0.21 |
| Dura | 67 | 18 | 0.21 | 0.22 | 0.12 | 0.37 | 0.17 | 0.14 | 0.01 | 0.09 |
| epidural vein | 69 | 7 | 0.09 | −0.18 | −0.45 | −0.05 | −0.01 | −0.65 | 0.09 | 0.09 |
| pia matter | 65 | 16 | 0.20 | 0.19 | 0.19 | 0.15 | 0.11 | 0.21 | 0.01 | 0.01 |
| nerve root inside spinal cord | 86 | 3 | 0.03 | −0.27 | −0.36 | 0.01 | 0.04 | −0.35 | 0.03 | 0.03 |
| nerve root outside spinal cord | 71 | 0 | 0.00 | −0.34 | −0.54 | −0.02 | 0.02 | −0.78 | 0.00 | 0.00 |
| inside spinal cord white matter | 76 | 26 | 0.25 | 0.26 | 0.32 | 0.18 | 0.12 | 0.36 | 0.01 | 0.07 |
| nerve root | 65 | 4 | 0.06 | −0.34 | −0.61 | −0.01 | 0.02 | −1.09 | 0.06 | 0.06 |
| AVERAGE | | | | | | | | | 0.04 | 0.07 |
| STDV | | | | | | | | | 0.04 | 0.05 |

Alternative Embodiment 2

In the second alternative embodiment we make first use of the same way as in alternative embodiment 1 to determine the scatter effect on the spectrum. To determine the lipid water ratio we make use the approximation that the effect of the absorption on the spectrum is proportional to $$S_{absorption}(\lambda) \approx \text{Exp}[-\alpha\sqrt{\mu_a(\lambda)}] \quad (5)$$

Apart from measuring the spectrum at the points $S_1$ and $S_2$ to determine the scattering contribution we measure again two point $S_3$ and $S_4$ but the location may be arbitrary as long as they are in the neighborhood of the points $S_1$ and $S_2$. For instance we can choose $S_3$ and $S_4$ to be located at 1195 nm and 1210 nm. Since we know the effect of the scattering we can remove the scattering according to $$S_1^a = S_1 + (S_2 - S_1)\left(\frac{(\lambda_4 - \lambda_1)}{(\lambda_2 - \lambda_1)}\right)$$

$$S_3^a = S_3 + (S_2 - S_1)\left(\frac{(\lambda_4 - \lambda_3)}{(\lambda_2 - \lambda_1)}\right)$$

$$S_4^a = S_4$$

$$A = \mu_a^w(\lambda_3) - \mu_a^w(\lambda_1)$$

$$B = \mu_a^l(\lambda_3) - \mu_a^l(\lambda_1)$$

$$C = \mu_a^w(\lambda_4) - \mu_a^w(\lambda_1)$$

$$D = \mu_a^l(\lambda_4) - \mu_a^l(\lambda_1)$$

$$Q = \left(\frac{\text{Ln}[S_3^a/S_1^a]}{\text{Ln}[S_4^a/S_1^a]}\right)^2$$

$$lw = \frac{QC - A}{B - QD}$$

$$\frac{lipids}{water + lipids} = \frac{lw}{1 + lw}$$

(6)

In Table II examples of this method, referred to as method 3, are given. The accuracy of this method 3 is less than that of method 2. Especially in cases where the amount of lipids is large deviations can be significant.

Alternative Embodiment 3

In the third alternative embodiment we make first use of the same way as in alternative embodiment 1 to determine the scatter effect on the spectrum. To determine the lipid water ratio we make use the approximation that the effect of the absorption on the spectrum is proportional to $$S_{absorption}(\lambda) \approx \text{Exp}[-\alpha\mu_a(\lambda)] \quad (7)$$

Apart from measuring the spectrum at the points $S_1$ and $S_2$ to determine the scattering contribution we measure again two point $S_3$ and $S_4$ but the location may be arbitrary as long as they are in the neighborhood of the points $S_1$ and $S_2$. For instance we can choose $S_3$ and $S_4$ to be located at 1195 nm and 1210 nm. Since we know the effect of the scattering we can remove the scattering according to $$S_1^a = S_1 + (S_2 - S_1)\left(\frac{(\lambda_4 - \lambda_1)}{(\lambda_2 - \lambda_1)}\right)$$

$$S_3^a = S_3 + (S_2 - S_1)\left(\frac{(\lambda_4 - \lambda_3)}{(\lambda_2 - \lambda_1)}\right)$$

$$S_4^a = S_4$$

$$A = \mu_a^w(\lambda_3) - \mu_a^w(\lambda_1)$$

$$B = \mu_a^l(\lambda_3) - \mu_a^l(\lambda_1)$$

$$C = \mu_a^w(\lambda_4) - \mu_a^w(\lambda_1)$$

$$D = \mu_a^l(\lambda_4) - \mu_a^l(\lambda_1)$$

$$Q = \left(\frac{\text{Ln}[S_3^a/S_1^a]}{\text{Ln}[S_4^a/S_1^a]}\right)$$

$$lw = \frac{QC - A}{B - QD}$$

$$\frac{lipids}{water + lipids} = \frac{lw}{1 + lw}$$

(8)

In Table II examples of this method 4 are given. The accuracy of this method 4 is less than that of method 2. Especially in cases where the amount of lipids is large deviations can be significant.

Alternative Embodiment 4

A further method is to consider the two points $S_3$ and $S_4$ as defined above and correct these for the scattering. Since $S_3$ differs only from $S_2$ by the variation in absorption due to lipids:

$$\Delta S_3 = S_3 - S_2 - \frac{23}{100.5}(S_2 - S_1) \quad (9)$$

$$\Delta \mu_a(3) = -0.1133 \text{ cm}^{-1}$$

Similar for $S_4$ but here the difference is due to the difference in absorption in water only:

$$\Delta S_4 = S_4 - S_2 - \frac{109}{100.5}(S_2 - S_1) \quad (10)$$

$$\Delta \mu_a(4) = 2.5879 \text{ cm}^{-1}$$

When we assume that the absorption is for small variation linear proportional to the absorption we can determine the absorption in the following way:

$$\frac{\Delta S_3}{\Delta S_4} = \frac{\Delta \mu_a(3)\text{lipids}}{\Delta \mu_a(4)\text{water}} \quad (11)$$

So we find $$lw = \frac{\Delta \mu_a(4) \Delta S_3}{\Delta \mu_a(3) \Delta S_4} \quad (12)$$

$$\frac{\text{lipids}}{\text{water} + \text{lipids}} = \frac{lw}{1 + lw}$$

Where lw denotes the lipid-water ratio. In Table II examples of this method 5 are given.

Alternative Embodiment 5

Various modifications of the above embodiments are possible, for instance taking other ways of approximating absorption (5) and (7). However, the way to remove the effect of scattering as proposed above is used. Using more than the four points mentioned above is possible to improve the outcome. For instance using an additional point between $S_3$ and $S_4$ could improve the outcome.

It is noticed, that by meticulously measuring the absorption spectra for water and lipids, respectively, and examining the spectra, specific sets of wavelengths have been identified as sets of wavelengths which satisfy that lambda_1 is substantially similar to an optical absorption coefficient for water at lambda_2 and an optical absorption coefficient for lipids at lambda_1 is substantially similar to an optical absorption coefficient for lipids at lambda_2. These wavelength sets comprise the sets of wavelengths {740.0 nm; 773.0 nm}, {955.0 nm; 1000.0 nm}, {1010.0 nm; 1128.5 nm}, {1150.5 nm; 1251.0 nm}, or {1380.9 nm; 1663.9 nm}, which are also given in Table III.

TABLE III

Absorption due to various components (water, lipids and blood constituents oxyhemoglobin HbO2 and haemoglobin Hb) at different wavelengths, of five different wavelength sets.

| Wavelength λ (nm) | Absorption $\mu_a$ H$_2$O (cm$^{-1}$) | Absorption $\mu_a$ lipids (cm$^{-1}$) | Absorption $\mu_a$ HbO2 (cm$^{-1}$) | Absorption $\mu_a$ Hb (cm$^{-1}$) | $\mu_a$ HbO$_2$/ $\mu_a$ lipids | $\mu_a$ Hb/ $\mu_a$ lipids | $\mu_a$ lipids/ $\mu_a$ H$_2$O |
|---|---|---|---|---|---|---|---|
| 740.0 | 0.02768 | 0.00654 | 2.40840 | 6.02580 | 368.2569 | 921.38 | 0.2363 |
| 773.0 | 0.02780 | 0.00653 | 2.62070 | 6.68370 | 401.3323 | 1023.5 | 0.2349 |
| 955.0 | 0.39115 | 0.02666 | 6.45760 | 3.03320 | 242.2206 | 113.8 | 0.0682 |
| 1000.0 | 0.39407 | 0.02654 | 5.52960 | 1.11660 | 208.3497 | 42.07 | 0.0673 |
| 1010.0 | 0.33480 | 0.04057 | 5.31810 | 0.98550 | 131.0845 | 24.29 | 0.1212 |
| 1128.5 | 0.33289 | 0.03974 | 1.66300 | 0.42730 | 41.84701 | 10.75 | 0.1194 |
| 1150.5 | 1.05000 | 0.23049 | 1.30600 | 0.44030 | 5.666189 | 1.910 | 0.2195 |
| 1251.0 | 1.05250 | 0.23855 | 0.51191 | 0.25794 | 2.145923 | 1.081 | 0.2267 |
| 1380.9 | 5.96328 | 0.71840 | 0.47882 | 0.36189 | 0.666509 | 0.5037 | 0.1205 |
| 1663.9 | 5.94766 | 0.69900 | 0.72523 | 0.54814 | 1.037525 | 0.7842 | 0.1175 |

Apparatus Embodiments

Below, some examples of embodiments are described that are able to detect tissue properties in a number of narrow wavelength bands, according to various embodiments described in the previous section.

FIG. 3 shows examples of apparatus embodiments in which filters are used to reach the required wavelength selectivity. Left (FIGS. 3A-C): filtered detectors. Right (FIGS. 3D-F): filtered light source. In FIGS. 3A-C the photo detector (PD) is filtered, while in FIGS. 3D-F the light source (S) is filtered.

Figure 3A:
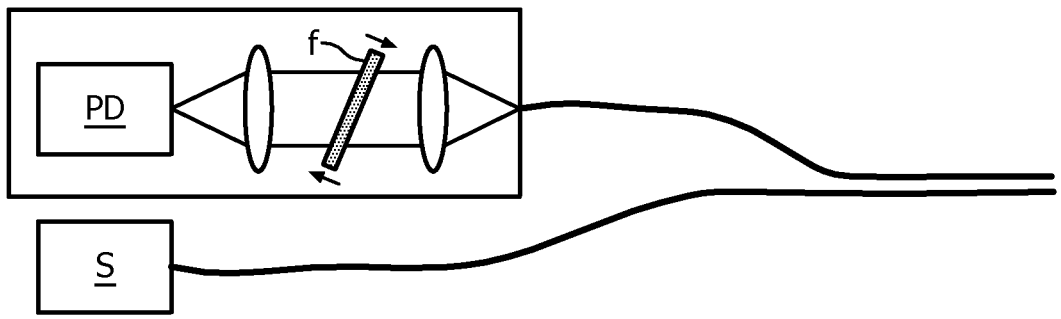
FIG. 3 shows apparatus embodiments based on filters.

In FIG. 3A, the required wavelength is selected by making use of the angular dependence of the narrow-band filter (f); by tilting the filter to the appropriate angle the required wavelength can be detected.

Figure 3B:
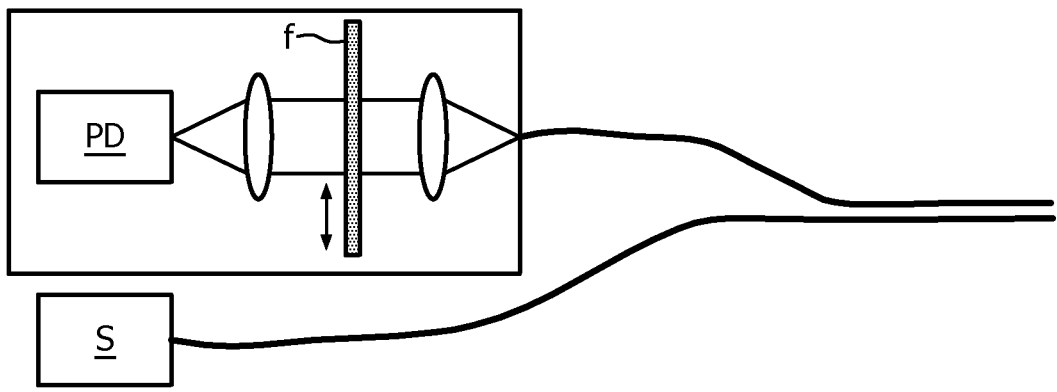

In FIG. 3B, use is made of a narrowband filter (f) of which the transmission wavelength varies as a function of position. The required wavelength is selected by changing the position at which the light beam impinges on the filter; e.g. by shifting the filter relative to the beam.

Figure 3C:
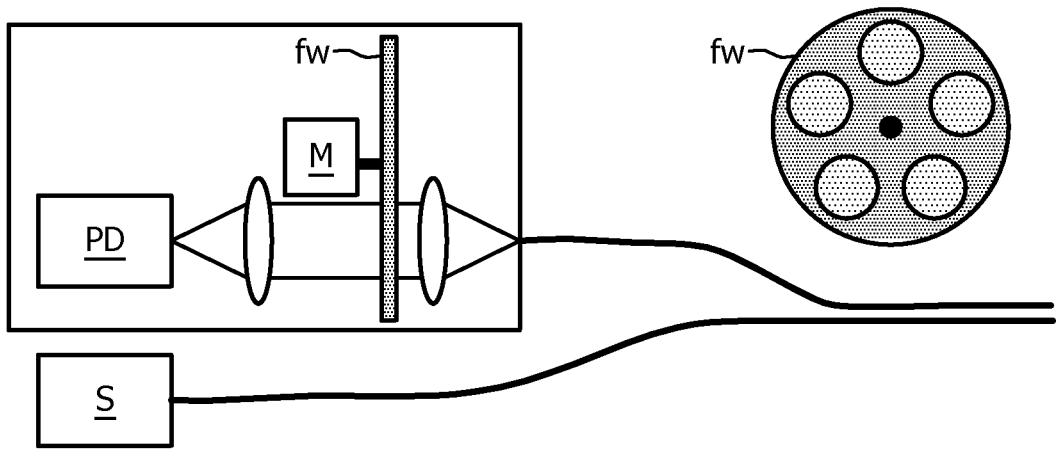

In FIG. 3C, a filter wheel (fw) containing narrowband filters at the required wavelengths is used. When the filter wheel is rotated by means of a motor (M) the appropriate wavelength can be selected. Instead of a wheel, a strip containing separate filters could, of course, also be used.

Figure 3D:
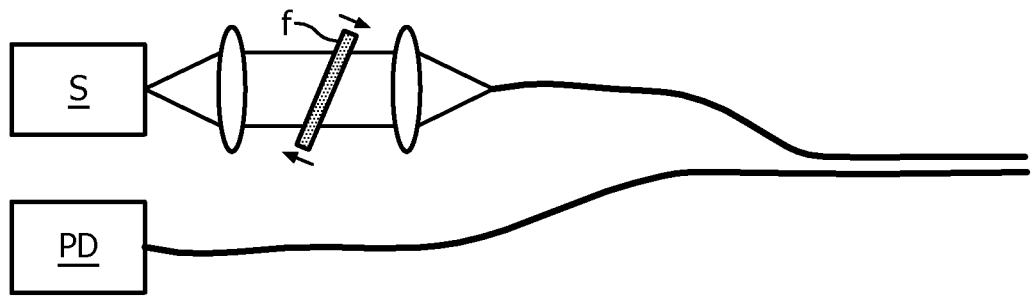
Figure 3E:
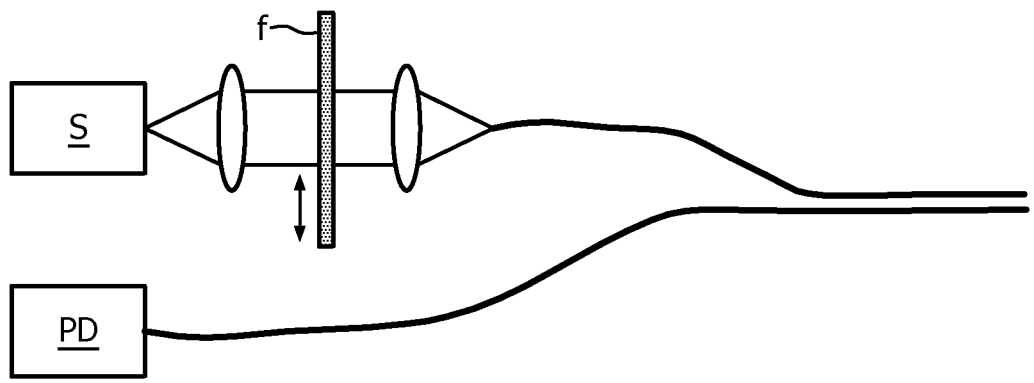
Figure 3F:
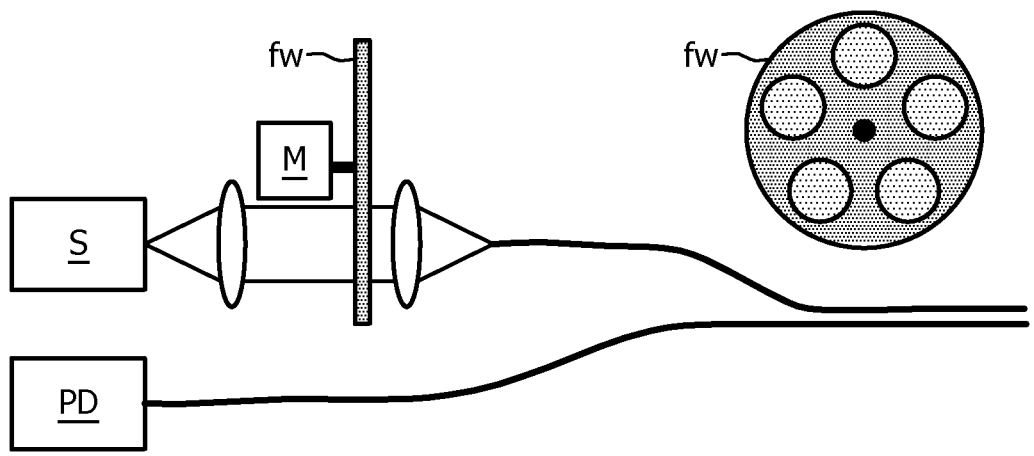

FIGS. 3D-F are similar to FIGS. 3A-C, respectively, except that now the light source (S) rather than the photo detector (PD) is being filtered.

FIG. 4 shows examples of apparatus embodiments in which the wavelength selectivity is reached by means of a dispersive element, e.g. a grating. In the figures a grating is used, but a prism could be used equally well. The grating (gr) diffracts light towards the photo detector (PD). The direction in which the light is diffracted depends on the wavelength; the position and size of aperture (a) in front of the detector determine the centre wavelength and the width of the wavelength range that are detected.

Figure 4A:
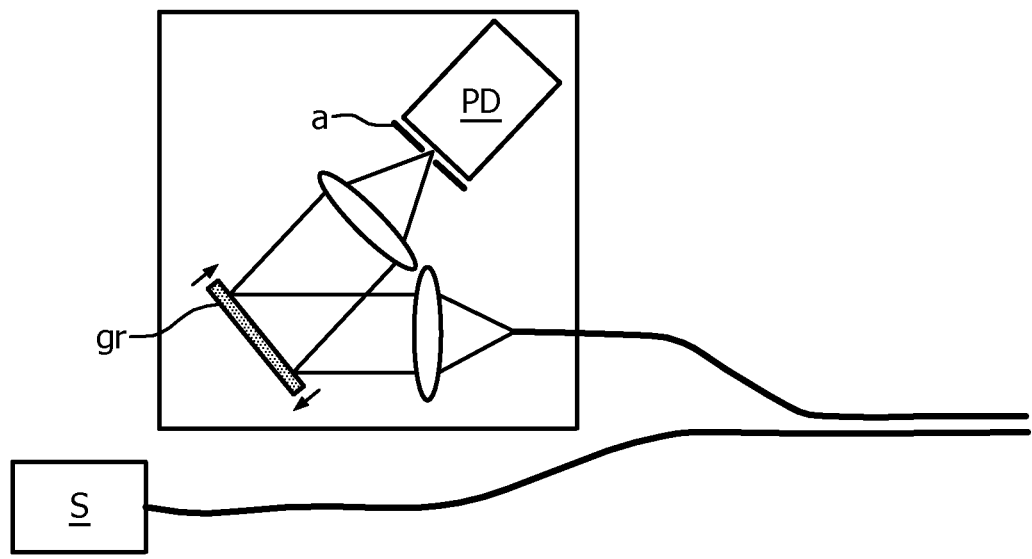
FIG. 4 shows apparatus embodiments based on wavelength selection by means of dispersive devices (e.g. gratings) and apertures.

In FIG. 4A, the wavelength is selected by tilting or rotating the grating (gr) while the aperture is stationary.

Figure 4B:
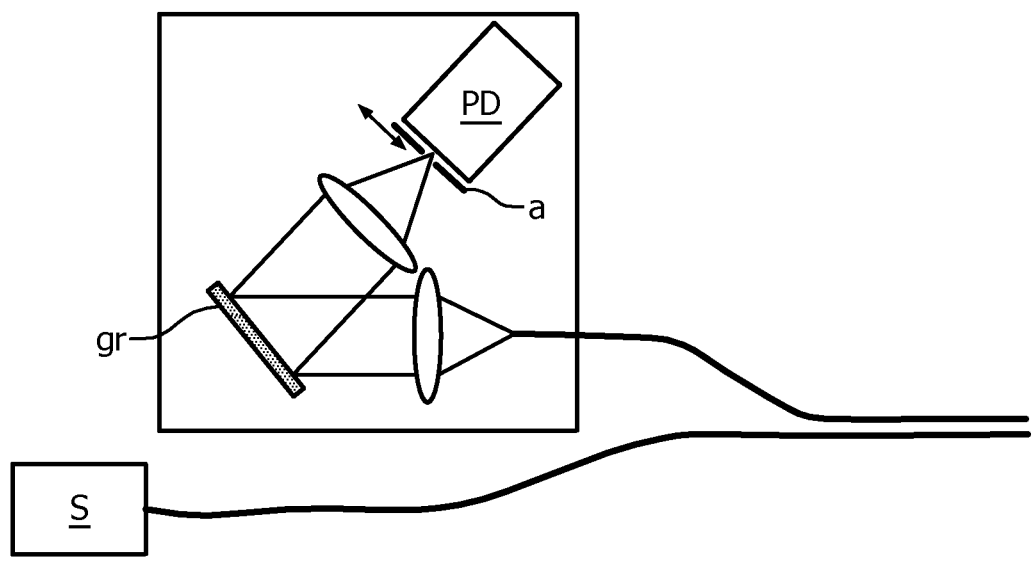

In FIG. 4B, the wavelength is selected by shifting the position of the aperture while the orientation of the grating (gr) is stationary. In case the sensitive area of the photo detector is smaller than the required shift of the aperture, it may be necessary to also shift the photo detector in conjunction with the aperture.

Figure 4C:
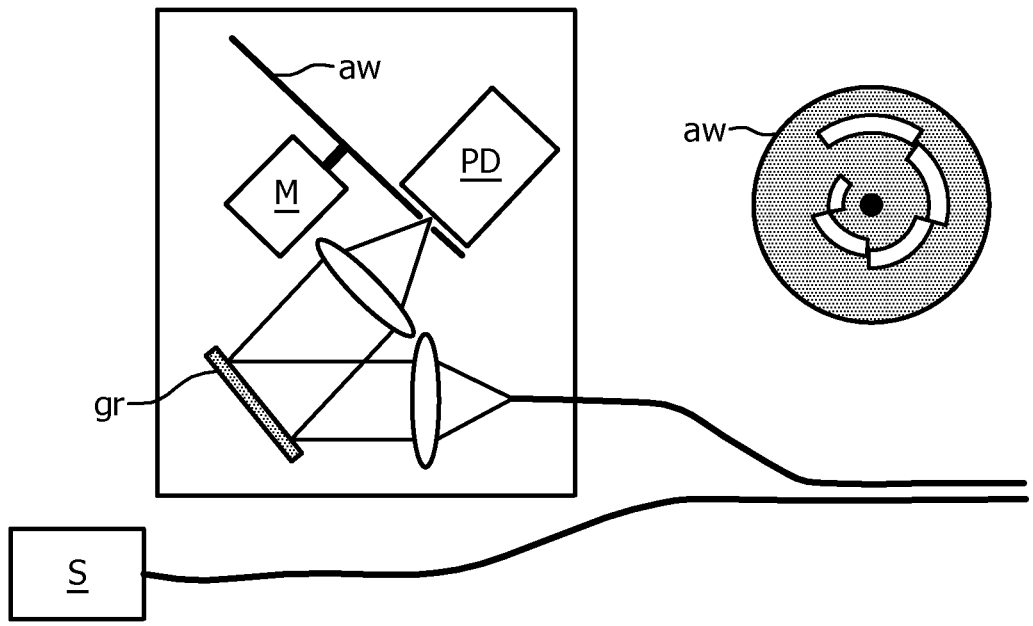

In FIG. 4C, the required change in position of the aperture is realized by rotating an aperture wheel (aw) that contains aperture slits at different radii, by means of a motor (M). In case the sensitive area of the photo detector is smaller than the spread in aperture radii on the aperture wheel (aw), optical means can be employed to lead the light transmitted through the apertures towards the photo detector.

Figure 4D:
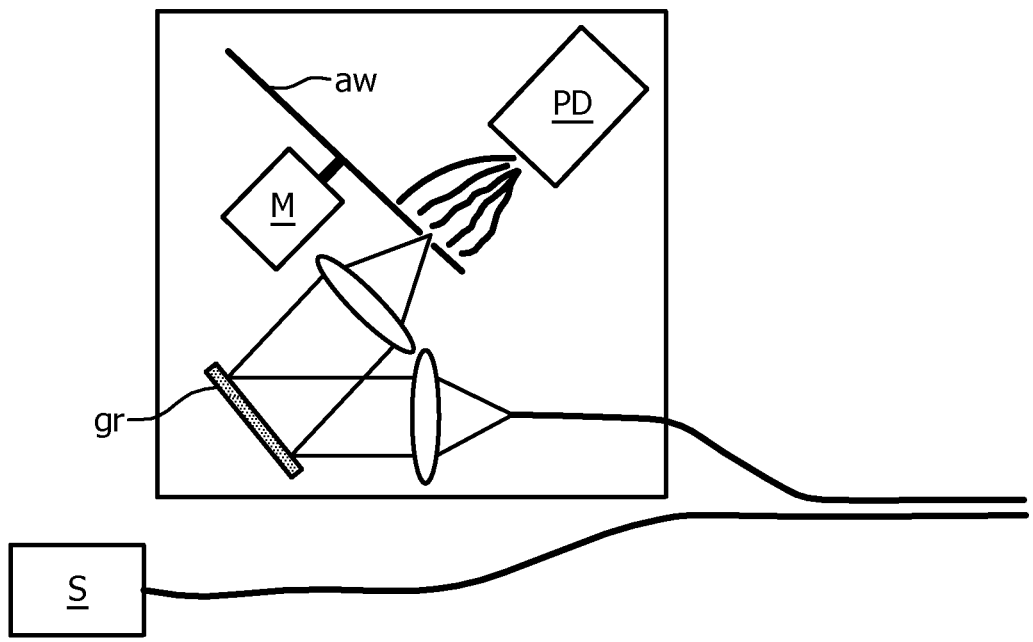

In FIG. 4D light guides (e.g., optical fibers) are used to this effect, but other means can also be used, e.g., by deflecting the light behind each aperture with a mirror towards the photo detector.

It is also possible to modulate the various wavelength bands with different modulation frequencies at the source and demodulate these at the detector, (this technique is described the published patent application WO2009/153719 which is hereby incorporated by reference in its entirety.

Various other modifications can be envisioned without departing from the scope of the invention for instance using more than on detector or using more than one light source with different wavelength band, such as Light Emitting Diodes (LEDs) or laser sources.

Figure 5:
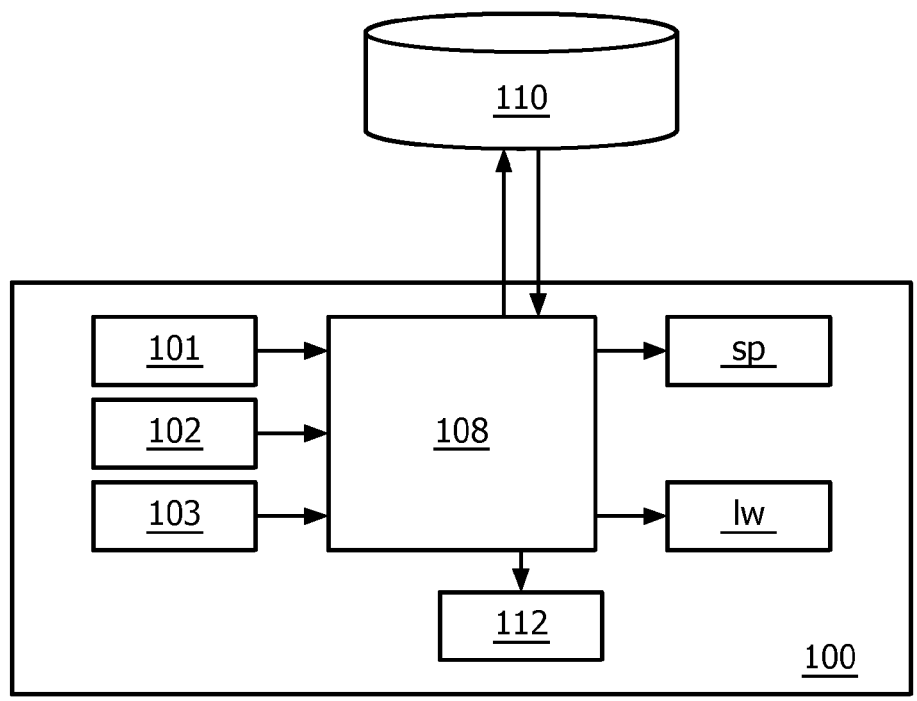
FIG. 5 shows a diagrammatic depiction of an apparatus according to an embodiment of the invention.

FIG. 5 shows an apparatus (100) according to an embodiment of the invention which comprises a processor (108) arranged for receiving information (101) derived from the first optical parameter measured at lambda_1, receiving information (102) derived from the second optical parameter measured at lambda_2, receiving information (103) derived from the third optical parameter measured at lambda_3, calculating a scattering parameter (sp) based on the information (101) derived from the first optical parameter and the information (102) derived from the second optical parameter, and calculating a lipid-water ratio (lw) based on information derived from the scattering parameter (sp) and information (103) derived from the third optical parameter. Furthermore, the shown apparatus is further arranged to access a database (110) comprising information regarding various tissue types, and identify which tissue type (112) or tissue types the sample is most likely to comprise, the identification is based on the lipid-water ratio and may further be based on other parameters, such as the scattering ratio (sp) or any one of the information (101), (102), (103) derived, respectively, from the first, second and third optical parameter.

Furthermore, a system may be provided for determining a lipid-water ratio in an associated sample, comprising an apparatus according to the first aspect, the system further comprising a database, such as the database (110) depicted in FIG. 5, comprising information regarding a lipid-water ratio of the sample. The database may further comprise information regarding various tissue types, so as to enable determination of which tissue type or tissue types the sample is most likely to comprise. The database may alternatively comprise information regarding foodstuffs in general, i.e. both from animals (and foodstuffs derived there from, e.g. milk and cheese) and vegetables (e.g. nuts and other lipid containing raw materials). In some embodiments a system may be provided which comprises a transmitter for transmitting a value representative of the lipid-water ratio. Having a transmitter may be advantageous in that the value representative of the lipid-water ratio can be transmitted to any recipient which is then enabled to make use of the lipid-water ratio. Such recipient may be any one of a user, a display, a computer or the like.

Figure 6:
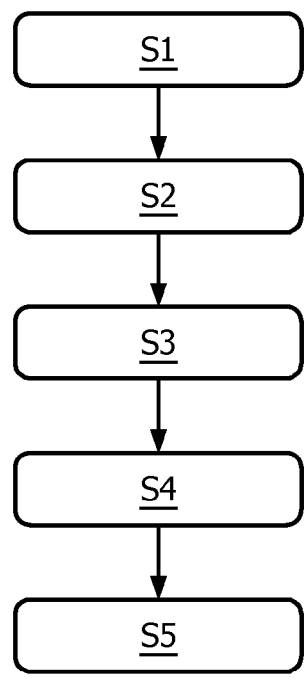
FIG. 6 is a flow chart of a method according to an aspect of the invention.

FIG. 6 is a flow chart of a method for determining a lipid-water ratio in a sample according to an aspect of the present invention. Such a method comprises the steps of:

measuring (S1) a first optical parameter at a first selected and distinct wavelength lambda_1, measuring (S2) a second optical parameter at a second selected and distinct wavelength lambda_2, measuring (S3) a third optical parameter at a third selected and distinct wavelength lambda_3, and determining (S4) a scattering parameter based on the first optical parameter and the second optical parameter, and determining (S5) a lipid-water ratio based on the scattering parameter and the third optical parameter wherein an optical absorption coefficient for water at lambda_1 is substantially similar to an optical absorption coefficient for water at lambda_2 and an optical absorption coefficient for lipids at lambda_1 is substantially similar to an optical absorption coefficient for lipids at lambda_2.

To sum up, the present invention relates to an apparatus, a method and a computer program for determining a lipid-water ratio and a scattering parameter of a sample. In particular, the invention relates to an apparatus comprising a light source and a detector arranged to measure an optical parameter at various wavelengths, where the wavelengths are selected so that at two of the wavelengths the absorption coefficients for both water and lipids are substantially identical. This enables determination of a scattering parameter. A further measurement at a third wavelength enables determination of a water-lipid ratio. According to a specific embodiment, the light source and the detector are arranged in relation to an interventional device, so as to be able to examine a tissue in terms of lipid-water ratio and scattering during an intervention.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An apparatus for determining a lipid-water ratio in an associated sample, comprising
a light source, and
a light detector,
the light source and the light detector being arranged to
measure an optical parameter of the sample at a limited number of selected and distinct wavelengths, and arranged to measure a first, second and third optical parameter at the selected and distinct wavelengths lambda_1, lambda_2 and lambda_3, respectively, wherein an optical absorption coefficient for water at lambda_1 is substantially similar to an optical absorption coefficient for water at lambda_2 and an optical absorption coefficient for lipids at lambda_1 is substantially similar to an optical absorption coefficient for lipids at lambda_2, and wherein the apparatus is configured to determine a lipid-water ratio of the sample based on the first and second optical parameters measured at lambda_1 and lambda_2 and the third optical parameter measured at lambda_3.

2. An apparatus according to claim 1, wherein the first selected wavelength lambda_1 and the second selected wavelength lambda_2 are chosen so as to enable disentangling of the contributions to the optical parameter from scattering and absorption.

3. An apparatus according to claim 1, wherein the apparatus is capable of determining a scattering parameter via a direct relation between the scattering parameter and the first and second optical parameters.

4. An apparatus according to claim 3, wherein the apparatus is further capable of determining a parameter indicative of freshness based on the scattering parameter.

5. An apparatus according to claim 1, wherein the apparatus further comprises a plurality of light sources with different wavelength bands and/or a plurality of light detectors with different wavelength bands, wherein two of the wavelength bands correspond to lambda_1 and lambda_2.

6. An apparatus according to claim 1, wherein the apparatus further comprises a processor arranged for
receiving information derived from the first optical parameter measured at lambda_1,
receiving information derived from the second optical parameter measured at lambda_2,
receiving information derived from the third optical parameter measured at lambda_3,
calculating a scattering parameter based on the information derived from the first optical parameter and the information derived from the second optical parameter, and
calculating a lipid-water ratio based on information derived from the scattering parameter and information derived from the third optical parameter.

7. An apparatus according to claim 6, wherein the apparatus is further arranged to access a database comprising information regarding various tissue types, and identify which tissue type or tissue types the sample is most likely to comprise, and wherein the identification is based on the lipid-water ratio.

8. An apparatus according to claim 1, wherein the wavelengths lambda_1 and lambda_2 are chosen to be substantially identical to any one of the sets of wavelengths {740.0 nm; 773.0 nm}, {955.0 nm; 1000.0 nm}, {1010.0 nm; 1128.5 nm}, {1150.5 nm; 1251.0 nm}, or {1380.9 nm; 1663.9 nm}.

9. An apparatus according to claim 1, wherein the light source and the light detector are arranged in relation to an interventional device, so as to be able to determine a lipid-water ratio of a sample in the vicinity of the interventional device.

10. An apparatus according to claim 1, wherein the apparatus is arranged for measuring an optical parameter at four different wavelengths including lambda_1, lambda_2 and lambda_3.

11. A system for determining a lipid-water ratio in an associated sample, comprising an apparatus according to claim 1, the system further comprising a database comprising information regarding a lipid-water ratio of the sample.

12. A method for determining a lipid-water ratio in a sample, the method comprising the steps of
measuring a first optical parameter at a first selected and distinct wavelength lambda_1,
measuring a second optical parameter at a second selected and distinct wavelength lambda_2,
measuring a third optical parameter at a third selected and distinct wavelength lambda_3, and
determining a scattering parameter based on the first optical parameter and the second optical parameter, and
determining a lipid-water ratio based on the scattering parameter and the third optical parameter
wherein an optical absorption coefficient for water at lambda_1 is substantially similar to an optical absorption coefficient for water at lambda_2 and an optical absorption coefficient for lipids at lambda_1 is substantially similar to an optical absorption coefficient for lipids at lambda_2.

13. A method according to claim 12, the method further comprising the step of
measuring a fourth optical parameter at a fourth selected and distinct wavelength lambda_4, the fourth optical parameter also being used in the step of determining a lipid-water ratio, wherein the third wavelength lambda_3 has substantially the same absorption coefficient for water as the absorption coefficient for water at lambda_1 and lambda_2, and the absorption coefficient for lipids at lambda_4 is substantially the same as the absorption coefficient for lipids at lambda_1 and lambda_2.

14. A method according to claim 12, wherein the lipid-water ratio is determined using any one of the steps of:
inserting measured optical parameters into a look-up table,
measuring further optical parameters and fitting a model to a number of the measured optical parameters, wherein the model includes the lipid-water ratio as an input parameter,
comparing a number of the measured optical parameters with an analytical approximation based on diffusion theory, and/or
comparing a number of the measured optical parameters with the result of a Monte Carlo calculation.

15. A computer program product being adapted to enable a computer system comprising at least one computer having data storage means associated therewith to operate a processor arranged for
receiving information derived from a first optical parameter measured at a first selected and distinct wavelength lambda_1,
receiving information derived from a second optical parameter measured at a second selected and distinct wavelength lambda_2,
receiving information derived from a third optical parameter measured at a third selected and distinct wavelength lambda_3,
calculating a scattering parameter based on the information derived from the first optical parameter and the information derived from the second optical parameter, and
calculating a lipid-water ratio based on information derived from the scattering parameter and information derived from the third optical parameter, wherein an optical absorption coefficient for water at lambda_1 is substantially similar to an optical absorption coefficient for water at lambda_2 and an optical absorption coefficient for lipids at lambda_1 is substantially similar to an optical absorption coefficient for lipids at lambda_2.

* * * * *